July 26, 1949. R. L. BYRUM Plant Pat. 857
ROSE PLANT
Filed Jan. 30, 1948
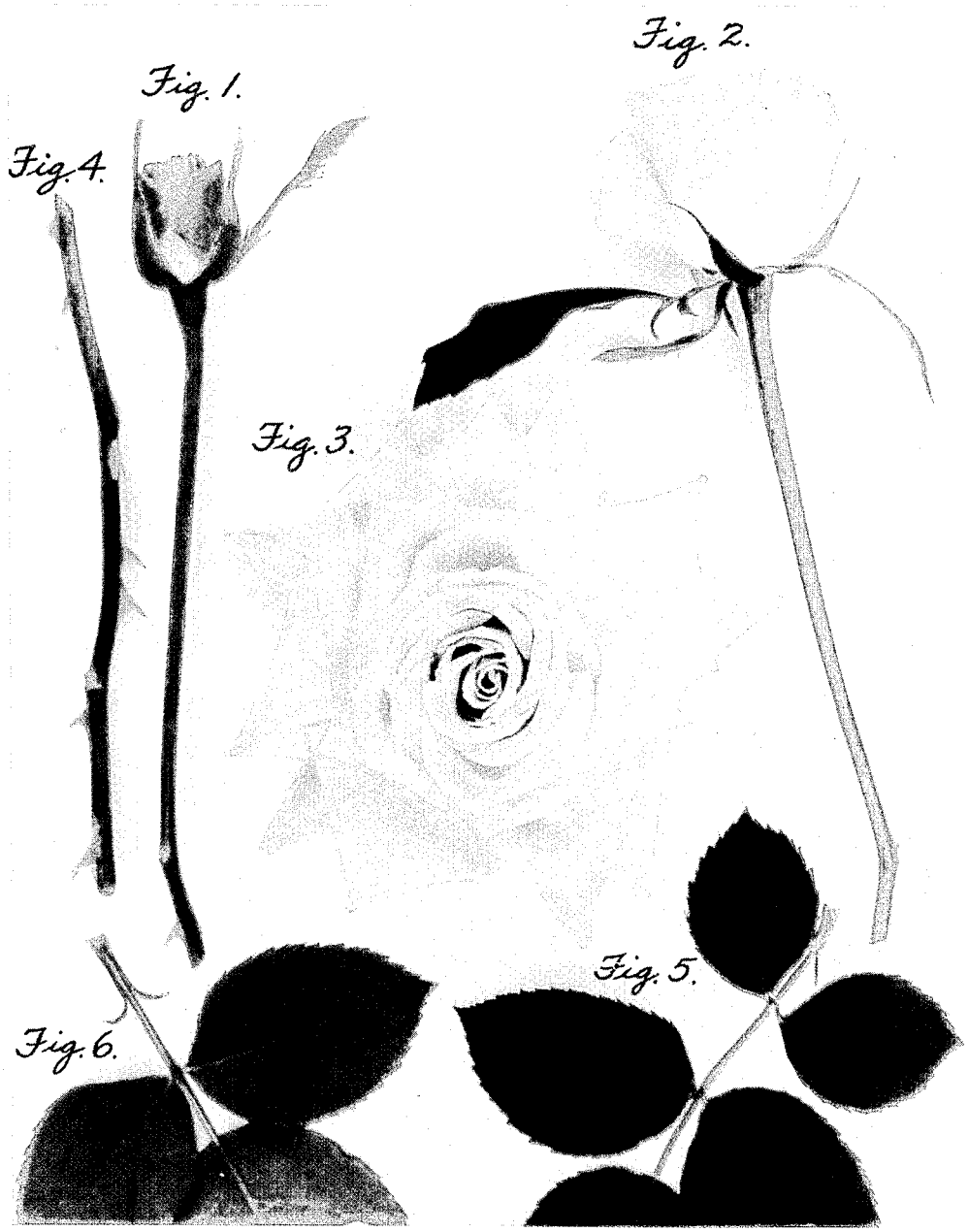
Inventor:
R. L. Byrum
By: Robert Cobb
Attorneys.

Patented July 26, 1949

Plant Pat. 857

UNITED STATES PATENT OFFICE

857

ROSE PLANT

Roy L. Byrum, Richmond, Ind., assignor to Joseph H. Hill Company, Richmond, Ind., a corporation of Indiana Application January 30, 1948, Serial No. 5,370

1 Claim. (Cl. 47—61)

The present invention relates to a new and distinct variety of rose plant, originated by the crossing of an unnamed seedling of medium red color ("Lucile Hill," Pl. Pat. #305×"Chieftain," Pl. Pat. #150) and the well-known variety "Pink Bountiful" (Pl. Pat. #601).

This new rose, a greenhouse forcing variety, is characterized as to novelty by the unique color and fragrance of its flowers. So far as I am aware, there is no other rose known to commerce today having this color or the penetrating characteristic of the tea fragrance, both of which characters are especially important in greenhouse forcing varieties.

Among the valuable features of novelty possessed by this improved variety that may be mentioned is the habit of this rose to break more freely from any eye, even on hard wood, than roses of the Briarcliff family; the slow opening or development from bud to full blown stages of the flowers, as compared with other types of roses, thus increasing its lasting quality; and finally, the striking uniformity of the coloring of the flowers.

Since there is no other rose, even including its parents, which is similar to the present variety, no helpful comparisons can be made herein. It is sufficient to specifically describe this new variety in detail as hereinafter set forth.

Asexual reproduction of this new variety shows the foregoing characteristics come true to form and are established.

In the drawing:

Fig. 1 is a view of a specimen bud of this variety as the calyx breaks;

Fig. 2 is a similar view as the first petal opens;

Fig. 3 is a top view of a full blown flower;

Fig. 4 is a specimen section of a main stem, showing the arrangement, shape and color of the thorns;

Fig. 5 is a top plan of a specimen of the foliage; and

Fig. 6 is a bottom plan of a foliage specimen.

The following is a detailed description of the new variety, color terminology being in accordance with Ridgway's Color Standards and Nomenclature, except where otherwise indicated to have ordinary dictionary significance.

Type: Bush; greenhouse; seedling; for cut flowers; not tested for garden use.

Class: Hybrid Tea.

Breeding: Seedling.

*Seed parent.*—Medium red rose whose seed parent was "Lucile Hill" (Pl. Pat. #305) and pollen parent "Chieftain" (Pl. Pat. #150).

*Pollen parent.*—"Pink Bountiful" (Pl. Pat. #601).

Propagation: Holds its distinguishing characteristics through succeeding propagations by cutting, grafting and budding.

*Flower*

Locality where grown: Richmond, Indiana.

Flowers borne: Singly to stem; on strong medium length stems.

Quantity of blooms: Abundant in greenhouse.

Continuity: Continuous.

Fragrance: Penetrating; tea.

Bud:

*Peduncle.*—Long; medium heavy; stiff; medium green; almost smooth; few hairs.

*Before calyx breaks.* — *Size* — medium. *Form*—short; pointed, with a conspicuous neck; with foliaceous appendages on the surface of the bud; with bristle-like foliaceous parts extending beyond the tip of the bud equal to one-fourth of its length.

*As calyx breaks.* — *Color* — Bordeaux, Plate XII.

*As first petal opens.* — *Size* — medium. *Form*—Long; pointed. *Color* — outside: Rose Red, Plate XII; inside: Rose Red, Plate XII.

*Opening.*—Opens up well.

Bloom: Size, when fully open, medium; 3″ to 4″.

*Petalage.*—Double; from 32 to 35 petals arranged regularly.

*Form.*—High center at first; petals remaining at first very tightly rolled outward; becoming later, at maturity, tightly rolled outward.

Petals: Thick; with inside satiny and outside shiny.

*Shape.*—Outside—obovate. Intermediate—obovate. Inside—obovate.

This description of a newly opened flower was made from a rose grown in a greenhouse in the month of November, at Richmond, Indiana:

*Color.—Outside petal*—outside surface: Tyrian Rose, Plate XII; inside surface: Rose Color, Plate XII, shaded with Tyrian Rose, Plate XII. *Intermediate petal* — outside: Tyrian Rose, Plate XII; inside surface: Rose Color, Plate XII, shaded with Tyrian Rose, Plate XII. *Inner petal*—outside surface: Tyrian Rose, Plate XII; inside surface: Rose Color, Plate XII, shaded with Tyrian Rose, Plate XII.

This description was made from a rose that was open for three days in a greenhouse in the month of November, at Richmond, Indiana:

*Color.—Outside petal*—outside surface: Rose Color, Plate XII; inside surface: Rose Color, Plate XII, shaded with Tyrian Rose, Plate XII. *Inside petal*—outside surface: Rose Color, Plate XII; inside surface: Rose Color, Plate XII, shaded with Tyrian Rose, Plate XII.

*General color effect.*—Newly opened flower—Rose Color, Plate XII, shaded with Tyrian Rose, Plate XII. Three days open—Rose Color, Plate XII.

*Behavior.*—In greenhouse, persist.

*Flower longevity.*—Cut roses grown in greenhouse kept at living room temperatures—4 to 5 days in November.

*Reproductive organs*

Stamens: Many; arranged regularly about pistils.
Filaments: Short; reddish; most with anthers.
Anthers: Small; yellow; all open at once.
Pollen: Moderate; gold.
Pistils: Medium number.
Styles: Uneven; short; thin; bunched.
Stigma: White.
Ovaries: Some protruding from calyx.
Hips: None have developed as yet.
Sepals: Permanent; short; spear-shaped; curled. *Color*—inside—Chromium Green, Plate XXXII, overlaid with a white fuzz; outside—Chromium Green, Plate XXXII.

*Plant*

Foliage:

*Leaves.*—Compound of 5 to 7 leaflets; abundant; medium size; heavy.

*Leaflets.*—Shape—elliptical with apex acute; margin simply serrate.

*Color.*—Mature—upper surface: Dark green; under surface: Moderately green. *Young*—upper surface: light bronze red; under surface: light bronze red.

*Rachis.* — Medium heavy. Upper side — grooved; hairy; under side—smooth; prickly.

*Stipules.*—Medium long; medium width; with medium long points turning out at an angle of less than 45°.

*Disease.*—Resistant to mildew and blackspot.

Growth:

*Habit.*—Upright.

*Growth.*—Vigorous.

*Canes.*—Medium heavy.

*Branches.* — Dull green. *Thorns* — several; medium length; hooked downward; with long, narrow base. *Prickles* — none. *Hairs*—none.

*Branches.* — Dull green. *Thorns* — several; medium length; hooked downward; with long, narrow base. *Prickles* — none. *Hairs*—none.

*New shoots.*—Bronze. *Thorns*—several; medium length; straight.

I claim:

A new and distinct variety of rose plant characterized as to novelty by the color of the flowers and uniformity of such coloring; the penetrating fragrance of said flowers; the habit of free breaking from any eye as compared with other varieties of the Briarcliff family; and the slow development of the flowers from bud to full blown stages, substantially as shown and described.

ROY L. BYRUM.

No references cited.